US011957513B2

(12) United States Patent
Sudol

(10) Patent No.: US 11,957,513 B2
(45) Date of Patent: Apr. 16, 2024

(54) NON-RECTANGULAR TRANSDUCER ARRAYS AND ASSOCIATED DEVICES, SYSTEMS, AND METHODS

(71) Applicant: KONINKLIJKE PHILIPS N.V., Eindhoven (NL)

(72) Inventor: Wojtek Sudol, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 477 days.

(21) Appl. No.: 17/271,115

(22) PCT Filed: Aug. 30, 2019

(86) PCT No.: PCT/EP2019/073255
§ 371 (c)(1),
(2) Date: Feb. 24, 2021

(87) PCT Pub. No.: WO2020/043898
PCT Pub. Date: Mar. 5, 2020

(65) Prior Publication Data
US 2021/0251604 A1    Aug. 19, 2021

Related U.S. Application Data

(60) Provisional application No. 62/725,785, filed on Aug. 31, 2018.

(51) Int. Cl.
*A61B 8/00* (2006.01)
*B06B 1/06* (2006.01)

(52) U.S. Cl.
CPC .......... *A61B 8/4455* (2013.01); *A61B 8/4483* (2013.01); *B06B 1/0622* (2013.01)

(58) Field of Classification Search
CPC ........................... A61B 8/4483; A61B 8/4494
See application file for complete search history.

(56) References Cited

U.S. PATENT DOCUMENTS 4,173,007 A     10/1979  McKeighen
2017/0299719 A1*  10/2017  Beers .................. G01S 7/52085

FOREIGN PATENT DOCUMENTS

WO     2018065405 A1     4/2018

OTHER PUBLICATIONS

International Search Report and Written Opinion of PCT/EP2019/073255, dated Nov. 29, 2019.

* cited by examiner

*Primary Examiner* — Colin T. Sakamoto
*Assistant Examiner* — Tommy T Ly

(57) ABSTRACT

The present disclosure advantageously describes ultrasound imaging arrays that comprise ergonomic, non-rectangular shapes, as well as associated systems and methods. Non-rectangular transducer arrays allow for ergonomic probe shapes that improve patient comfort, maneuverability of the ultrasound device, and operator workflow. For example, an ultrasound imaging device can include an array of acoustic elements comprising a non-rectangular perimeter. The array includes a plurality of active elements configured to emit ultrasound energy and receive echoes corresponding to the emitted ultrasound energy, and a plurality of buffer elements surrounding the plurality of active elements at the non-rectangular perimeter of the array of acoustic elements. An edge seal comprising a sealing material is positioned at least partially around the plurality of buffer elements, and a buffer element of the plurality of buffer elements is spaced from at least one other buffer element by the sealing material of the edge seal.

14 Claims, 15 Drawing Sheets

NON-RECTANGULAR TRANSDUCER ARRAYS AND ASSOCIATED DEVICES, SYSTEMS, AND METHODS

TECHNICAL FIELD

The present disclosure relates generally to ultrasound imaging and, in particular, to techniques for fabricating imaging components including a transducer array with non-rectangular shapes, and associated devices and systems.

BACKGROUND

Ultrasound imaging is frequently used to obtain images of internal anatomical structures of a patient. Ultrasound systems typically comprise an ultrasound transducer probe that includes a transducer array coupled to a probe housing. The transducer array is activated to vibrate at ultrasonic frequencies to transmit ultrasonic energy into the patient's anatomy, and then receive ultrasonic echoes reflected or backscattered by the patient's anatomy to create an image. Such transducer arrays may include various layers, including some with piezoelectric materials, which vibrate in response to an applied voltage to produce the desired pressure waves. These transducers may be used to transmit and receive ultrasonic pressure waves through the various tissues of the body. The various ultrasonic responses may be further processed by an ultrasonic imaging system to display the various structures and tissues of the body.

A transducer array typically includes a rectangular one-dimensional or two-dimensional matrix array of acoustic elements. In some aspects, rectangular ultrasound transducer arrays can pose challenges for an ultrasound technician. For example, in cardiac imaging (e.g., echocardiography), an external ultrasound probe may be positioned and precisely aligned between a patient's ribs to obtain images of the patient's heart. This can be difficult to do with an ultrasound probe that comprises a rectangular array of acoustic elements, because one or more corners of the array may restrict movement and alignment of the ultrasound probe between the patient's ribs and/or cause discomfort for the patient during the imaging procedure.

SUMMARY

The present disclosure advantageously describes ultrasound imaging arrays that comprise ergonomic, non-rectangular shapes, as well as associated systems and methods. In one aspect, a non-rectangular array, which can also be referred to as a non-perpendicular array, can include one or more sealing materials around a perimeter of the array that forms an edge seal to provide structural integrity to less stable acoustic elements at or near the perimeter of the array. For example, a sealing material can be applied before, during, or after forming kerfs in an acoustic stack, where the kerfs are formed to divide the acoustic stack into individual acoustic elements. The sealing material can support and/or strengthen vulnerable areas of the acoustic stack while the kerfs are formed. In some aspects, non-rectangular transducer arrays allow for ergonomic probe shapes that improve patient comfort, maneuverability of the ultrasound device, and operator workflow.

In one aspect, an ultrasound imaging device includes an array of acoustic elements comprising a non-rectangular perimeter. The array of acoustic elements further includes a plurality of active elements configured to emit ultrasound energy and receive echoes corresponding to the emitted ultrasound energy, and a plurality of buffer elements surrounding the plurality of active elements at the non-rectangular perimeter of the array of acoustic elements. The device further includes an edge seal comprising a sealing material positioned at least partially around the plurality of buffer elements, wherein a buffer element of the plurality of buffer elements is spaced from at least one other buffer element by the sealing material of the edge seal.

In some embodiments, the non-rectangular perimeter comprises a curved segment. In some embodiments, the non-rectangular perimeter comprises a polygon. In some embodiments, each buffer element of a first portion of the plurality of buffer elements comprises a non-rectangular profile, the first portion of the plurality of buffer elements at an outer edge of the array of acoustic elements. According to some aspects, each buffer element of a second portion of the plurality of buffer elements comprises a rectangular profile, and the second portion of the plurality of buffer elements is spaced from the outer edge of the array of acoustic elements. According to other aspects, the edge seal includes a first sealing material in direct contact with the non-rectangular perimeter of the array of acoustic elements, the first sealing material comprising a plurality of kerfs, and a second sealing material positioned around the first sealing material and disposed within the plurality of kerfs of the first sealing material. In some embodiments, the device further includes a processor chip coupled to a surface of the array of acoustic elements, wherein the processing chip comprises a non-perpendicular perimeter that aligns with the non-perpendicular perimeter of the array of acoustic elements. In another embodiment, the device further includes a housing, and the array of acoustic elements is coupled to the housing.

According to another aspect of the present disclosure, a method for manufacturing an ultrasound imaging device includes removing material from a perimeter of an acoustic stack such that the acoustic stack comprises a non-rectangular perimeter, forming a first plurality of kerfs in the acoustic stack in a first direction, depositing a first sealing material at the non-rectangular perimeter of the acoustic stack, allowing the first sealing material to enter the first plurality of kerfs; curing the first sealing material, and forming a second plurality of kerfs in the acoustic stack and the first sealing material in a second direction to form an array of acoustic elements.

In some embodiments, removing material from the perimeter of the acoustic stack comprises forming a curved segment. In other embodiments, removing material from the perimeter of the acoustic stack comprises forming a polygonal segment. In some aspects, allowing the first sealing material to enter the first plurality of kerfs comprises waiting for the first sealing material to advance between about 150 microns and about 250 microns into the acoustic stack. In another aspect, the first sealing material comprises an epoxy, and curing the first sealing material comprises directing ultraviolet light to the epoxy. In some embodiments, the method further includes depositing a second sealing material around the first sealing material, allowing the second sealing material to enter the second plurality of kerfs, and curing the second sealing material.

In some embodiments, the method further includes removing material from a processing chip such that the processing chip comprises a non-perpendicular perimeter, and coupling the processing chip to the acoustic stack such that the non-perpendicular perimeter of the processing chip aligns with the non-perpendicular perimeter of the acoustic stack. In still other embodiments, the method further includes coupling the array of acoustic elements to a housing.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
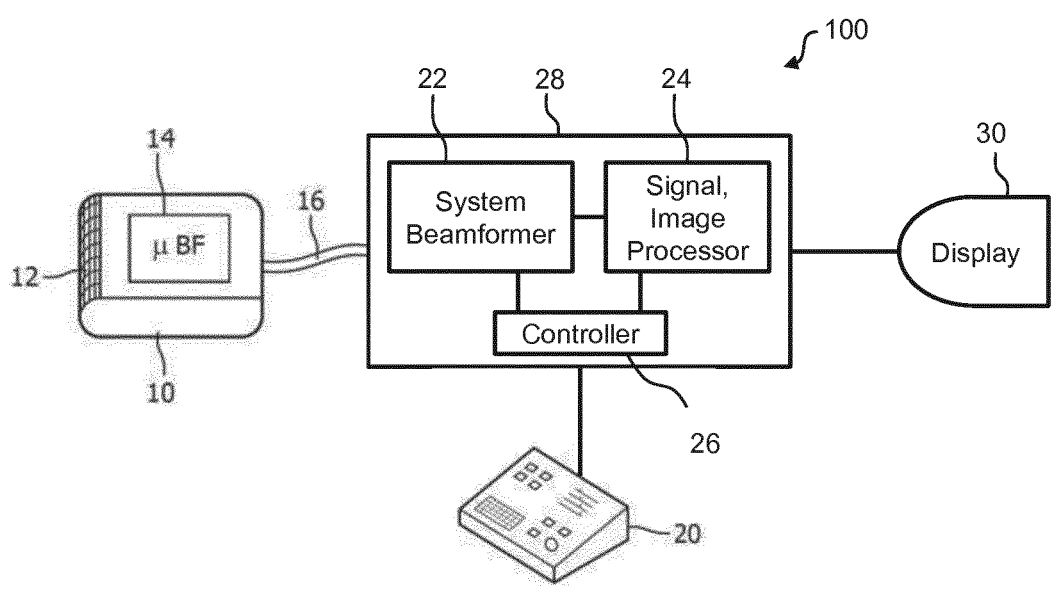
FIG. 1 is a schematic diagram of an ultrasound imaging system according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the ultrasound devices are described in terms of external imaging probes, it is understood that it is not intended to be limited to this application. The system is equally well suited to any application requiring imaging of an anatomy. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In FIG. 1, an ultrasound system 100 according to embodiments of the present disclosure is shown in block diagram form. An ultrasound probe 10 has a transducer array 12 comprising a plurality of ultrasound transducer elements or acoustic elements. In some instances, the array 12 may include any number of acoustic elements. For example, the array 12 can include between 1 acoustic element and 1000 acoustic elements, including values such as 2 acoustic elements, 4 acoustic elements, 36 acoustic elements, 64 acoustic elements, 128 acoustic elements, 300 acoustic elements, 812 acoustic elements, and/or other values both larger and smaller. In some instances, the acoustic elements of the array 12 may be arranged in any suitable configuration, such as a linear array, a planar array, a curved array, a curvilinear array, a circumferential array, an annular array, a phased array, a matrix array, a one-dimensional (1 D) array, a 1.x dimensional array (e.g., a 1.5 D array), or a two-dimensional (2 D) array. The array of acoustic elements (e.g., one or more rows, one or more columns, and/or one or more orientations) can be uniformly or independently controlled and activated. The array 12 can be configured to obtain one-dimensional, two-dimensional, and/or three-dimensional images of patient anatomy.

While the present disclosure refers to external ultrasound imaging using an external ultrasound probe configured for imaging while positioned adjacent to and/or in contact with the patient's skin, it is understood that one or more aspects of the present disclosure can be implemented in any suitable array-based ultrasound imaging system. For example, aspects of the present disclosure can be implemented in intraluminal ultrasound imaging systems using an intracardiac (ICE) echocardiography catheter and/or a transesophageal echocardiography (TEE) probe, intravascular ultrasound (IVUS) imaging catheters, and/or transthoracic echocardiography (TTE) imaging device in some embodiments.

Referring again to FIG. 1, the acoustic elements of the array 12 may comprise piezoelectric/piezoresistive elements, lead zirconate titanate (PZT), piezoelectric micromachined ultrasound transducer (PMUT) elements, capacitive micromachined ultrasound transducer (CMUT) elements, and/or any other suitable type of acoustic elements. The acoustic elements of the array 12 are in communication with (e.g., electrically coupled to) electronic circuitry 14. In some embodiments, such as the embodiment of FIG. 1, the electronic circuitry 14 can comprise a microbeamformer (μBF). In other embodiments, the electronic circuitry comprises a multiplexer circuit (MUX). The electronic circuitry 14 is located in the probe 10 and communicatively coupled to the transducer array 12. In some embodiments, one or more components of the electronic circuitry 14 can be positioned in the probe 10. In some embodiments, one or more components of the electronic circuitry 14, can be positioned in a processor 28, or processing system. In some aspects, some components of the electronic circuitry 14 are positioned in the probe 10 and other components of the electronic circuitry 14 are positioned in the processor 28. The electronic circuitry 14 may comprise one or more electrical switches, transistors, programmable logic devices, or other electronic components configured to combine and/or continuously switch between a plurality of inputs to transmit signals from each of the plurality of inputs across one or more common communication channels. The electronic circuitry 14 may be coupled to elements of the array 12 by a plurality of communication channels. The electronic circuitry 14 is coupled to a cable 16, which transmits signals including ultrasound imaging data to the processor 28.

In the processor 28, the signals are digitized and coupled to channels of a system beamformer 22, which appropriately delays each signal. The delayed signals are then combined to form a coherent steered and focused receive beam. System beamformers may comprise electronic hardware components, hardware controlled by software, or a microprocessor executing beamforming algorithms. In that regard, the beamformer 22 may be referenced as electronic circuitry. In some embodiments, the beamformer 22 can be a system beamformer, such as the system beamformer 22 of FIG. 1, or it may be a beamformer implemented by circuitry within the ultrasound probe 10. In some embodiments, the system beamformer 22 works in conjunction with a microbeamformer (e.g., electronic circuitry 14) disposed within the probe 10. The beamformer 22 can be an analog beamformer in some embodiments, or a digital beamformer in some embodiments. In the case of a digital beamformer, the system includes A/D converters which convert analog signals from the array 12 into sampled digital echo data. The beamformer 22 generally will include one or more microprocessors, shift registers, and or digital or analog memories to process the echo data into coherent echo signal data. Delays are effected by various means such as by the time of sampling of received signals, the write/read interval of data temporarily stored in memory, or by the length or clock rate of a shift register as described in U.S. Pat. No. 4,173,007 to McKeighen et al., the entirety of which is hereby incorporated by reference herein. Additionally, in some embodiments, the beamformer can apply appropriate weight to each of the signals generated by the array 12. The beamformed signals from the image field are processed by a signal and image processor 24 to produce 2 D or 3 D images for display on an image display 30. The signal and image processor 24 may comprise electronic hardware components, hardware controlled by software, or a microprocessor executing image processing algorithms. It generally will also include specialized hardware or software which processes received echo data into image data for images of a desired display format such as a scan converter. In some embodiments, beamforming functions can be divided between different beamforming components. For example, in some embodiments, the system 100 can include a microbeamformer located within the probe 10 and in communication with the system beamformer 22. The microbeamformer may perform preliminary beamforming and/or signal processing that can reduce the number of communication channels required to transmit the receive signals to the processor 28.

Control of ultrasound system parameters such as scanning mode (e.g., B-mode, M-mode), probe selection, beam steering and focusing, and signal and image processing is done under control of a system controller 26 which is coupled to various modules of the system 100. The system controller 26 may be formed by application specific integrated circuits (ASICs) or microprocessor circuitry and software data storage devices such as RAMs, ROMs, or disk drives. In the case of the probe 10, some of this control information may be provided to the electronic circuitry 14 from the processor 28 over the cable 16, conditioning the electronic circuitry 14 for operation of the array as required for the particular scanning procedure. The user inputs these operating parameters by means of a user interface device 20.

In some embodiments, the image processor 24 is configured to generate images of different modes to be further analyzed or output to the display 30. For example, in some embodiments, the image processor can be configured to compile a B-mode image, such as a live B-mode image, of an anatomy of the patient. In other embodiments, the image processor 24 is configured to generate or compile an M-mode image. An M-mode image can be described as an image showing temporal changes in the imaged anatomy along a single scan line.

It will be understood that the processor 28 can comprise hardware, such as a computer processor, application-specific integrated circuit (ASIC), field-programmable gate array (FPGA), capacitors, resistors, and/or other electronic devices, software, or a combination of hardware and software. In some embodiments, the processor 28 is a single computing device. In other embodiments, the processor 28 comprises separate computer devices in communication with one another.

Figure 2:
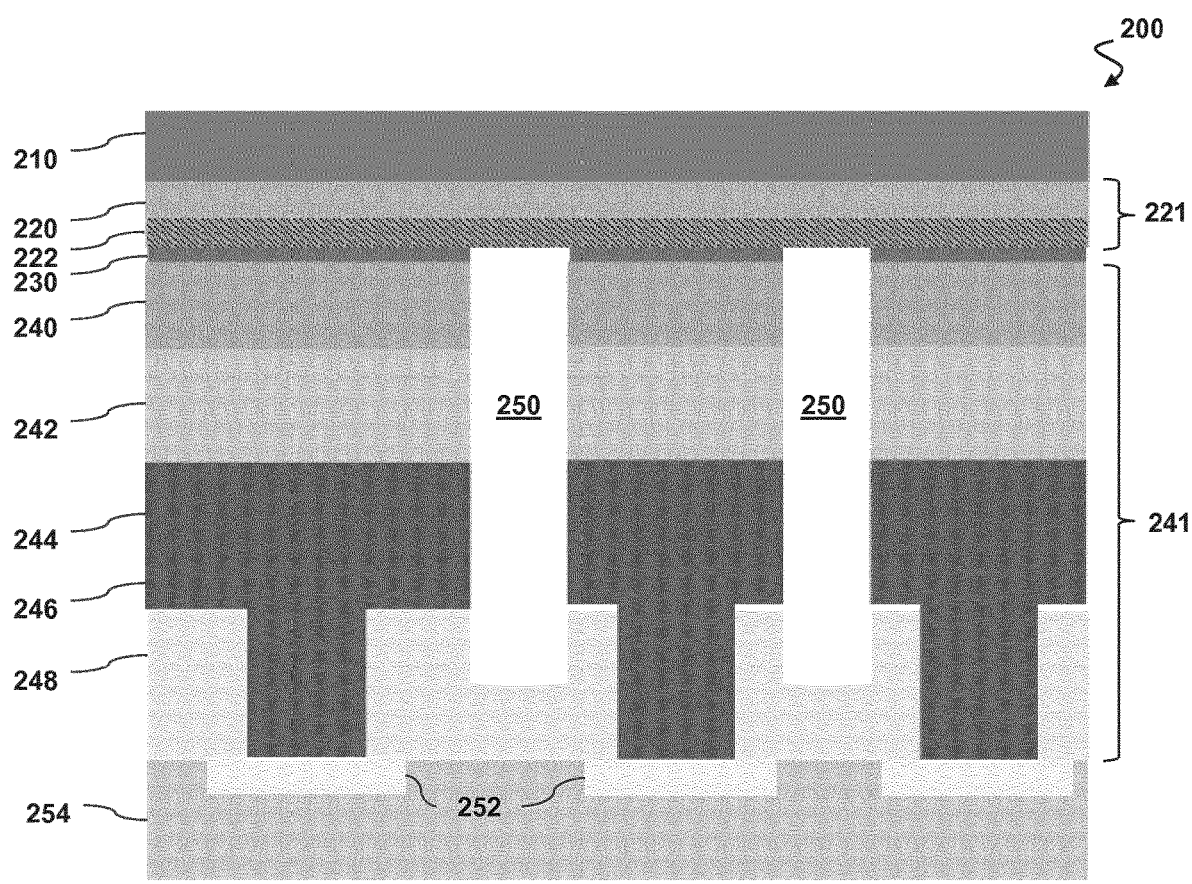
FIG. 2 is a cross sectional view of individual elements of a transducer array formed of an acoustic stack according to embodiments of the present disclosure.

FIG. 2 is an exemplary illustration of a portion of an acoustic element array 200, according to aspects of the present disclosure. In some embodiments, the array 200 may be implemented as the transducer in the ultrasound imaging device. For example, in the illustrated embodiment of FIG. 2, the array 200 includes three acoustic elements 241. In general, the array 200 can include any suitable number of acoustic elements 241. The acoustic element 241 can be formed of a plurality of material layers (e.g., layers 240, 242, 244, 246, and/or other suitable layers). In some instances, the acoustic element 241 can be referenced as a pillar, such as a pillar including multiple material layers. The acoustic element array 200 may also include an acoustic matching layer 210, a ground plane 221, and a substrate 254.

Additional processes, steps, and features relating to forming acoustic stacks and acoustic arrays are described in U.S. Provisional App. No. 62/641,582, filed Mar. 12, 2018, the entirety of which is hereby incorporated by reference.

In some embodiments, the substrate 254 is a semiconductor substrate that may form the base of the acoustic element array 200. The substrate 254 may include materials such as silicon, silicon dioxide, aluminum oxide, germanium, and/or other suitable materials. In some embodiments, the substrate 254 is a flexible substrate, such as a polymer substrate, a polyimide substrate, e.g., Kapton®, and/or other suitable material. The material of the substrate 254 can be selected based on the application in some instances. For example, the flexible substrate can be used for a one-dimensional array. The flexible substrate can also be used for a two-dimensional or matrix array in some instances. A semiconductor substrate, with, e.g., electrical interconnects contained therein, can be implemented in a two-dimensional or matrix array configured for three-dimensional imaging.

Figure 3:
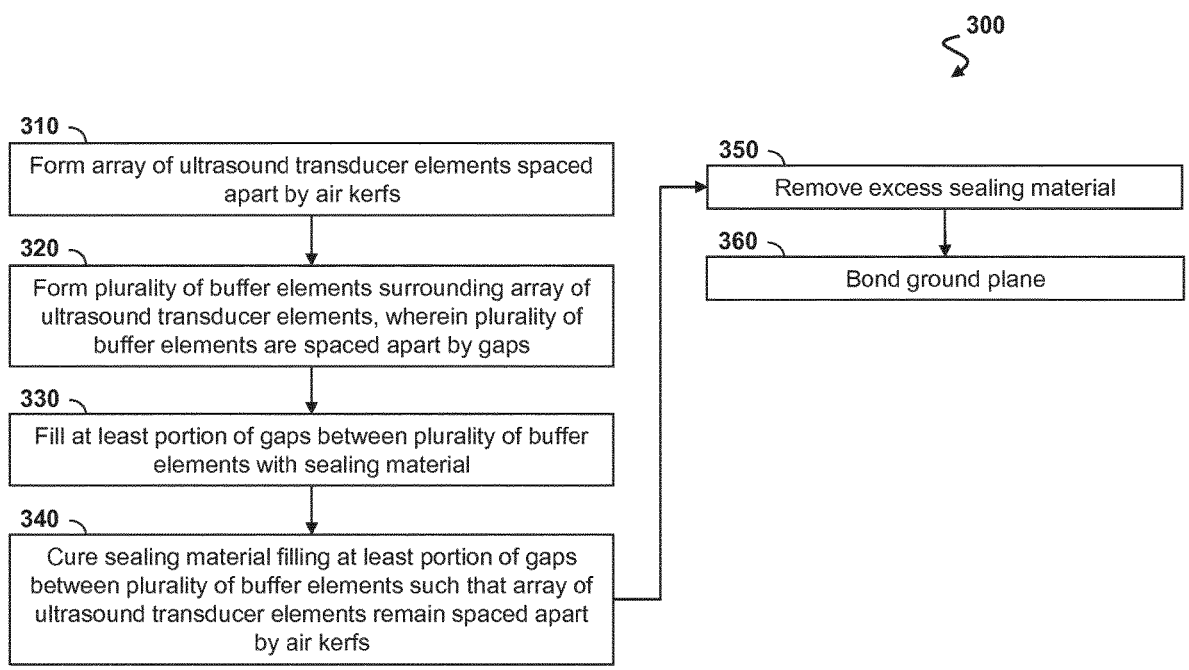
FIG. 3 is a flow diagram of a method for manufacturing a transducer array according to embodiments of the present disclosure.

In some embodiments, the acoustic matching layer 210 includes a pliable film, such as a polyurethane film. The matching layer 210 may be cast on the ground plane 221. A bottom surface of the matching layer 210 may be in physical contact with the top surface of the ground plane 221 without an adhesive layer in between the matching layer and the ground plane 221. In some embodiments, the matching layer 210 has a thickness of about 10 µm-200 µm and/or other suitable values, both larger and smaller. In some embodiments, the thickness of the matching layer 210 can be selected based on the acoustic center frequency of the transducer 220 (FIG. 2) or the array 200 (FIG. 3). For example, low frequency transducer designs (e.g., center frequency of about 0.5 MHz-5 MHz) can have about 100 µm-200 µm matching layer thickness, mid-range frequency transducer designs (e.g., center frequency of about 5 MHz-10 MHz) can have about 50 µm-150 µm matching layer thickness, and high frequency transducer designs (e.g., center frequency >10 MHz) can have about 10 µm-100 µm matching layer thickness. In some embodiments, the combination of the matching layer 210 and the ground plane 221 may be referred to as a metalized matching layer. The matching layer 210 can be or be part of an acoustic lens of the ultrasound imaging device. In some instances, the array 200 includes multiple matching layers 210, such as different matching layers with different acoustic properties (e.g., acoustic impedance).

In some embodiments, the ground plane 221 includes an upper layer 220 and a lower layer 322. The upper layer 220 may include one or more polymers, such as polyether, polyester, or polyimide. In some embodiments, the upper layer 220 has a thickness of about 3-12 µm. In other embodiments, the upper layer 220 has a thickness of about 1-10 µm, 2-5 µm, 5-10 µm, and/or other suitable values, both larger and smaller. The lower layer 222 may include an electrode formed from a metal such as gold, silver, copper, aluminum, platinum, and/or other suitable materials. In some embodiments, the lower layer 222 has a thickness of about 3000 Å. In other embodiments, the lower layer 222 has a thickness of about 1000 Å-9000 Å, 2000 Å-3000 Å µm, or 4000 Å-6000 Å, and/or other suitable values, both larger and smaller. The electrode layer 222 can be configured to carry electrical current. In some embodiments, the thickness of the electrode layer 222 can be selected based on the amount of current being transmitted. In some instances, the thickness of the electrode layer 222 can be the same while the thickness of other layers (e.g., matching layer 210, upper layer 220) changes in different ultrasound devices. For example, the thickness of the electrode layer 222 can be the same while the thickness of the matching layer 210 changes according to the center frequency in different ultrasound devices. In some embodiments, the bottom surface of the matching layer 210 is in direct physical contact with the top surface of the upper layer 220 of the ground plane 221. In some embodiments, the matching layer 210 is cast directly on the ground plane 221. For example, the matching layer 210 may be cast on the ground plane 221 in a solvent casting process by depositing a liquid mixture with solvent and dissolved material on the ground plane 221 and then removing the solvent. Casting techniques such as the "doctor blade" technique may be used to cast the matching layer 210 on the ground plane. Other casting techniques for depositing the matching layer 210 on the ground plane 221 are also contemplated, including spin coating, drop casting, sputtering, printing, spray coating, blade coating, solution shearing, and other techniques.

The attachment of the matching layer 210 to the ground plane 221 without adhesive may offer improved imaging performance compared to existing methods for forming transducers. Furthermore, the method of casting the matching layer 210 directly on the ground plane 221 offers manufacturing benefits. For example, the matching layer 210 is cast on the ground plane 221 before attaching the ground plane to the one or more acoustic elements 241. Since layers within the one or more acoustic elements 241 may be sensitive to high temperature and pressures, combining the matching layer 210 with the ground plane 221 separately may avoid damage to the one or more acoustic elements 241. Furthermore, casting the matching layer 210 directly on the ground plane 221 may result in flatter layers than existing methods because the matching layer 210 and ground plane 221 are not offset by imperfections in the layers within the one or more acoustic elements 241 during manufacturing. The improved flatness may offer better imaging performance of the completed ultrasound transducers. Additionally, the matching layer 210 and ground plane 221 may be prefabricated on a large scale which may lower manufacturing costs and allow inspection of the matching layer 210 and ground plane 221 before integration with more expensive components with the one or more acoustic elements 241. The ability to inspect earlier in the process may help to avoid unnecessary waste of expensive components.

The ground plane 221 may be attached to the one or more acoustic elements 241. In some embodiments, the ground plane 221 is configured to provide an electrical ground path for the layers of the acoustic elements 241. Each of the one or more acoustic elements 241 may include any combination of layers, such as a second matching layer 240, piezoelectric element 242, third matching layer 244 (or de-matching layer), and bump 246 (which may include graphite and/or other suitable conductive material). The acoustic element 241 may also include one or more of an underfill 248 and bond pads 252 (which may include gold and/or other suitable conductive material). In some embodiments, the ground plane 221 and matching layer 210 wrap around a portion of the layers of the one or more acoustic elements 241. For example, the ground plane 221 and matching layer 210 may wrap around the edges of the one or more acoustic elements 241, such that the ground plane 221 is in contact with an outer sidewall of the one or more acoustic elements 241.

During manufacturing, an acoustic stack including multiple layers (layers 240, 242, 244, 246 and/or other suitable layers) may be formed on the substrate 254. The acoustic stack is then diced, which forms the individual acoustic elements 241 spaced from one another by gaps or kerfs 250. In the embodiment of FIG. 2, the kerfs 250 are air-filled kerfs, or more simply, air kerfs. However, in other embodiments, the kerfs 250 can include any suitable type of kerf, such as a material-filled kerf. In some embodiments, the ground plane 221 is attached to the one or more acoustic elements 241 with an adhesive layer 230 disposed between the bottom surface of the ground plane and the top surface of the one or more acoustic elements 241. In particular, the lower layer 322 of the ground plane 221 may be attached to the one or more acoustic elements 241. The ground plane 221 and matching layer 210 may be disposed over multiple acoustic elements 241 and over the kerfs 250 between the acoustic elements 241.

Dividing the acoustic stack 200 into individual acoustic elements by forming kerfs is further explained below with respect to FIGS. 3-10. The acoustic array resulting from the kerfs is typically coupled to and encased in a housing filled with an encapsulating material. The encapsulating material can easily infiltrate into the air kerfs between the acoustic elements causing the air kerfs to be completed filled or partially filled instead of non-filled. One approach to protecting the air kerfs is to wrap all surfaces or sides of the array with a sealing film. However, the sealing film increases the footprint of the imaging component, which may not be desirable since catheters are space-limited. In addition, the wrapping of the ground plane may not completely seal the sides or surfaces of the array structure from infiltration of cleaning fluids, epoxies, or window material that are applied in subsequent fabrication process steps. In that regard, in some aspects, it can be beneficial to apply an edge seal around an imaging array that comprises air kerfs in order to seal the array.

Figure 4:
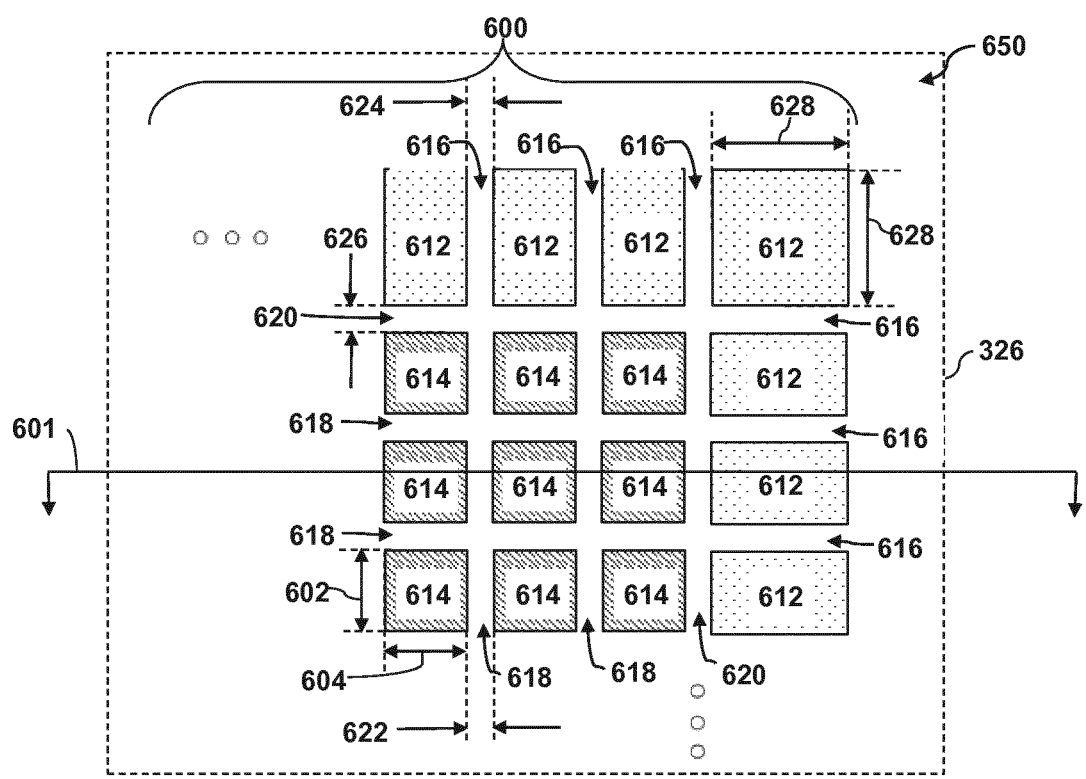
FIG. 4 is a top view of an array structure coupled to an integrated circuit (IC) layer in a stage of manufacturing according to embodiments of the present disclosure.
Figure 5:
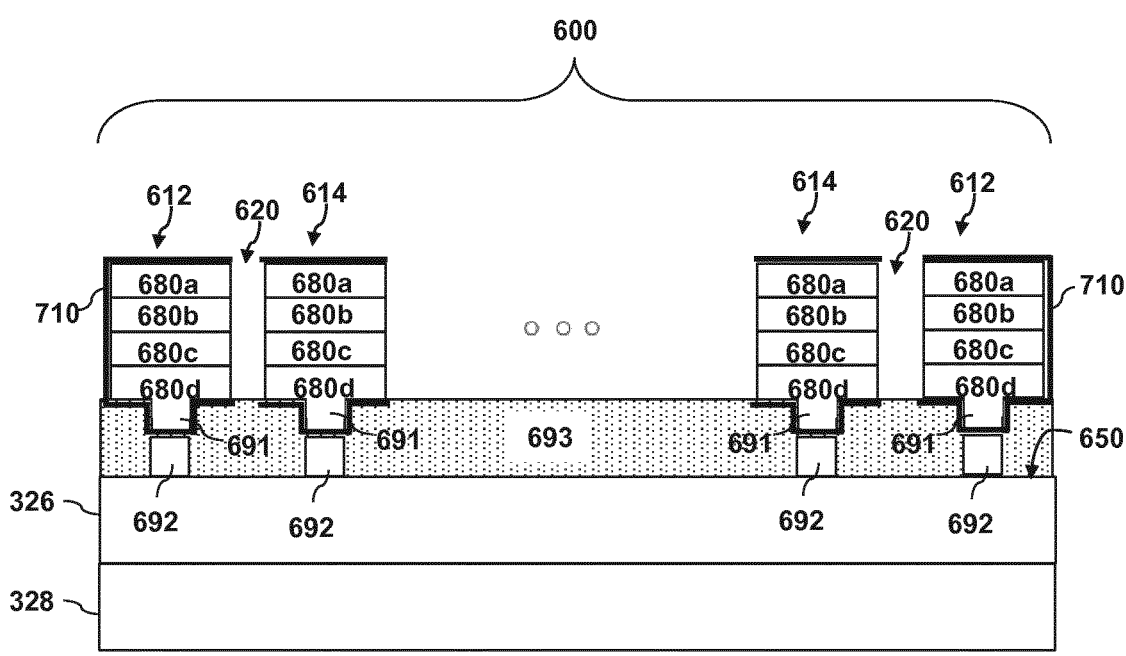
FIG. 5 is a cross-sectional view of an array structure coupled to an IC layer in a stage of manufacturing according to embodiments of the present disclosure.
Figure 6:
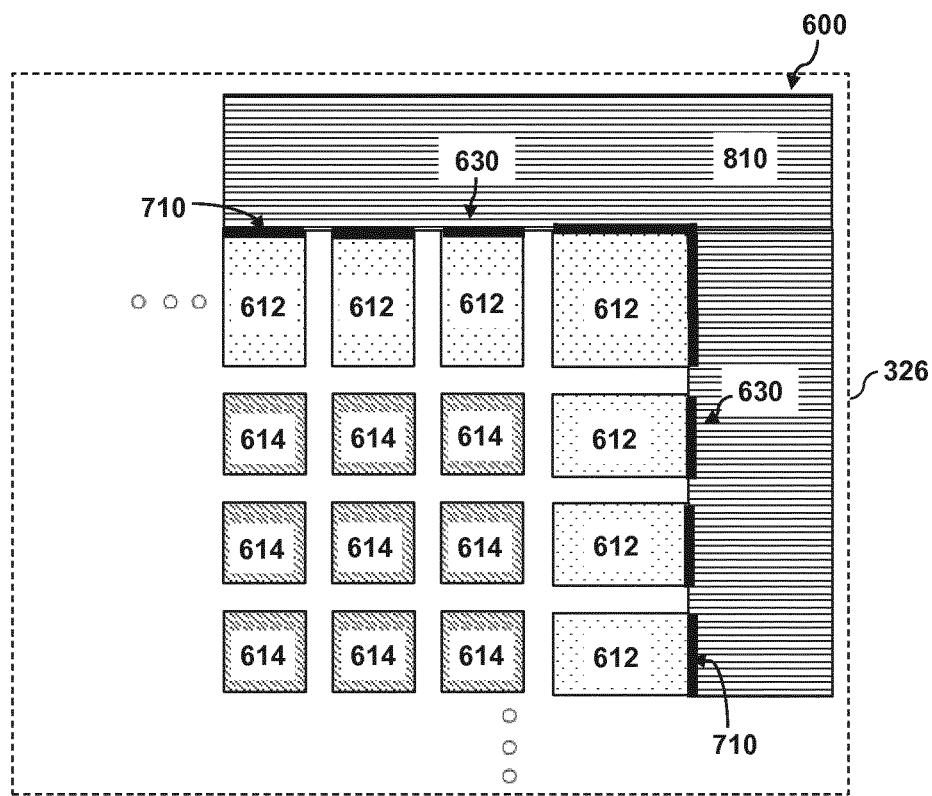
FIG. 6 is a top view of an array structure coupled to an IC layer in a stage of manufacturing according to embodiments of the present disclosure.
Figure 7:
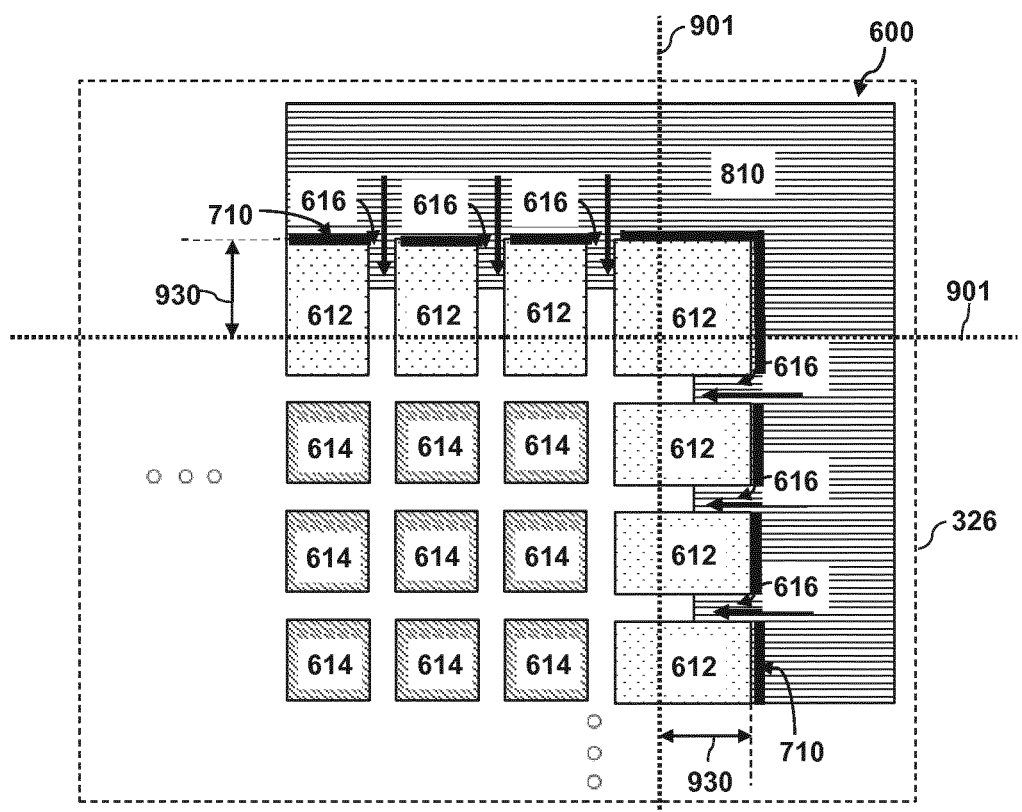
FIG. 7 is a top view of an array structure coupled to an IC layer in a stage of manufacturing according to embodiments of the present disclosure.
Figure 8:
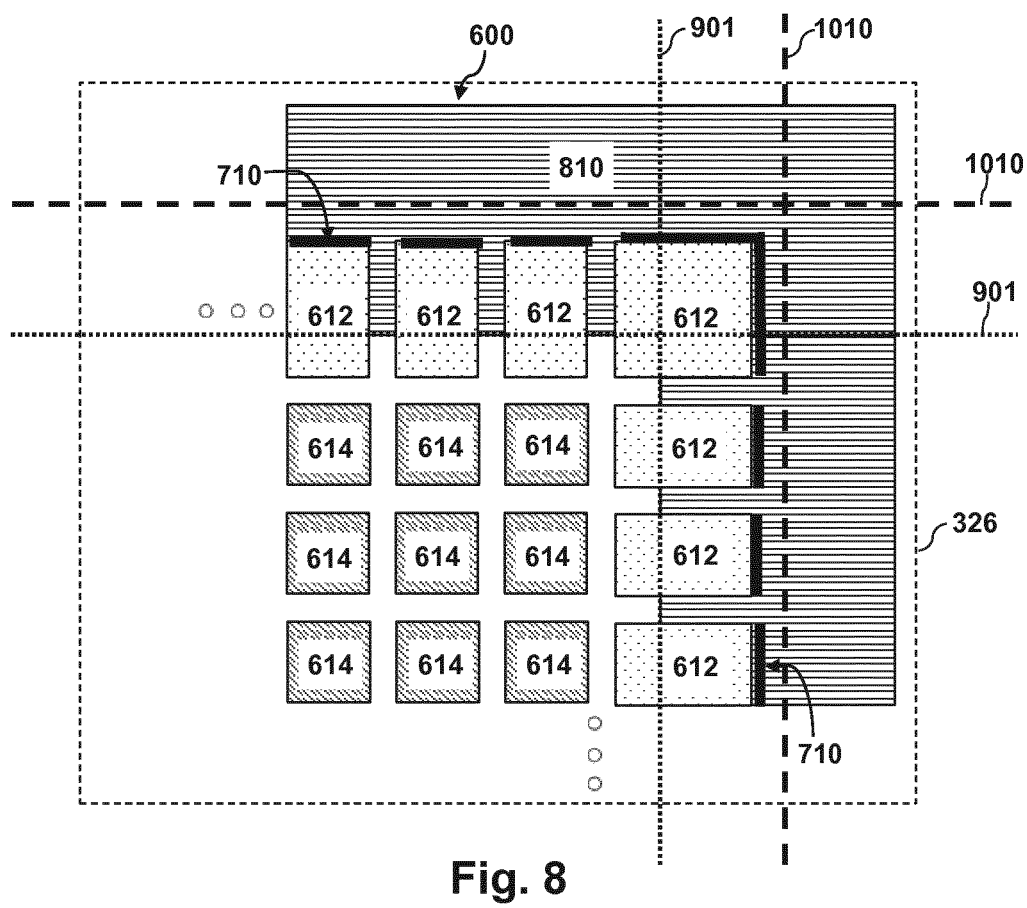
FIG. 8 is a top view of an array structure coupled to an IC layer in a stage of manufacturing according to embodiments of the present disclosure.
Figure 9:
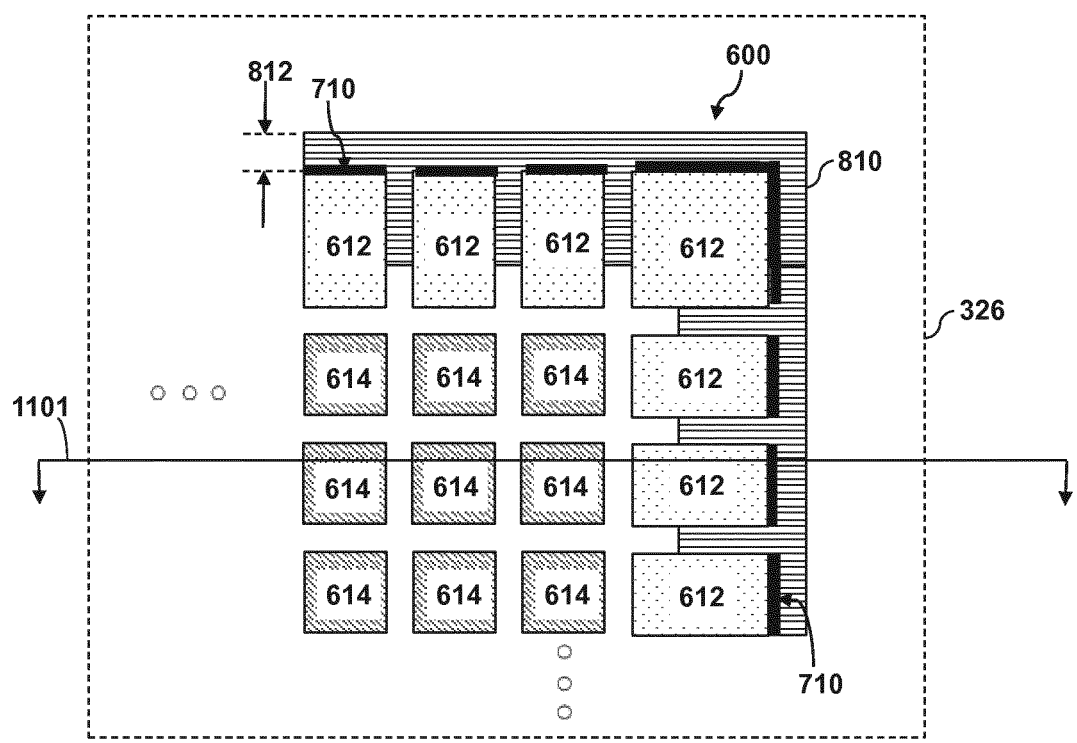
FIG. 9 is a top view of an array structure coupled to an IC layer in a stage of manufacturing according to embodiments of the present disclosure.
Figure 10:
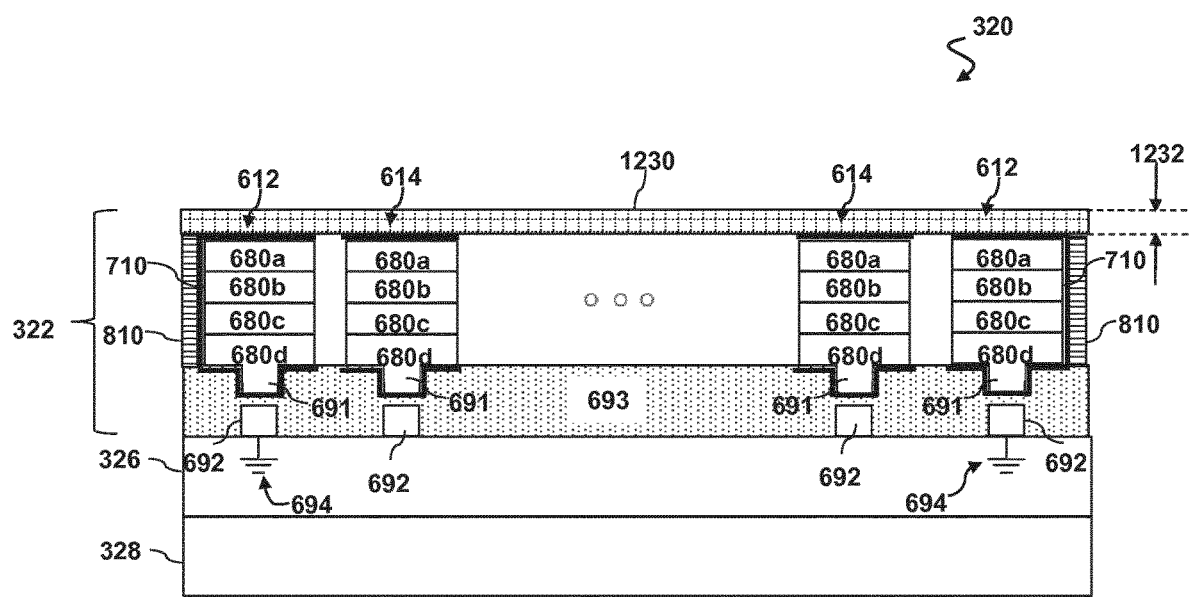
FIG. 10 is a cross-sectional view of an array structure coupled to an IC layer in a stage of manufacturing according to embodiments of the present disclosure.

A method 300 of manufacturing a transducer array is described with reference made to FIGS. 3-10. FIG. 3 is a flow diagram of a method 300 of manufacturing a transducer array, or imaging component, according to embodiments of the present disclosure. It is understood that additional steps can be provided before, during, and after the steps of method 300, and some of the steps described can be replaced or eliminated for other embodiments of the method. The steps of the method 300 can be carried out by a manufacturer of a catheter. FIG. 4 is a top view of an array structure 600 coupled to the IC layer 326 in a stage of manufacturing according to embodiments of the present disclosure. FIG. 5 is a cross-sectional view of the array structure 600 coupled to the IC layer 326 in a stage of manufacturing according to embodiments of the present disclosure. FIG. 6 is a top view of the array structure 600 sealed with a sealing material 810 in a stage of manufacturing according to embodiments of the present disclosure. FIG. 7 is a top view of the array structure 600 under a wicking process in a stage of manufacturing according to embodiments of the present disclosure. FIG. 8 is a top view of the array structure 600 after the wicking process is completed in a stage of manufacturing according to embodiments of the present disclosure. FIG. 9 is a top view of the array structure 600 after excess sealing material is removed in a stage of manufacturing according to embodiments of the present disclosure. FIG. 10 is a cross-sectional view of the imaging component including the array structure 600 in a stage of manufacturing according to embodiments of the present disclosure.

Additional processes, steps, and features relating to forming transducer arrays are described in U.S. Provisional App. No. 62/403,267, filed Oct. 3, 2016, and U.S. Provisional App. No. 62/434,568, filed Dec. 15, 2016, each of which is hereby incorporated by reference.

Referring to the step 310 of the method 300 and FIGS. 4 and 5, in an embodiment, an array of acoustic elements 614 separated by air kerfs 618 is formed, for example, using a machining or dicing process or any suitable process. The acoustic elements 614 form part of an array structure 600 shown in in FIGS. 4 and 5.

Referring to the step 320 of the method 300 and FIGS. 4 and 5, in an embodiment, a plurality of buffer elements 612 surrounding the array of acoustic elements 614 are formed. The plurality of buffer elements 612 is separated by gaps 616. The buffer elements 612 do not include transducer functionalities. The buffer elements 612 do not emit ultrasound energy when activated. The buffer elements 612 can provide array uniformity and function as a buffer to protect the acoustic elements 614, as described in greater detail herein. The buffer elements 612 form part of the array structure 600.

FIG. 4 illustrates a top view of the array structure 600 bonded to a top plane 650 of the IC layer 326. The array structure 600 can be uniformly shaped and can have a rectangular shape or a square shape. As shown, the acoustic elements 614 are arranged in rows and columns. The buffer elements 612 are positioned on the outer-most rows and outer-most columns of the array structure 600 surrounding the acoustic elements 614. The buffer elements 612 define the sides of the array structure 600. The buffer elements 612 are separated from the acoustic elements 614 by air kerfs 620. In some embodiments, the acoustic elements 614 and the buffer elements 612 can be uniformly spaced. Thus, the air kerfs 618 and 620 and the gaps 616 can have substantially similar widths and can be aligned to each other.

Dimensions of the array structure 600 may vary in different embodiments. In some embodiments, the acoustic elements 614 can have lengths 602 between about 90 μm to about 130 μm and widths 604 between about 90 μm to about 130 μm. The widths 622 of the air kerfs 618, the widths 624 of the gaps 616, and the widths 626 of the air kerfs 620 can be between about 18 μm to about 30 μm. The buffer elements 612 can be sized to provide a buffering region with at least a depth 628 of about 100 μm for the array structure 600.

FIG. 5 illustrates a cross-sectional view of the array structure 600 coupled to the IC layer 326 taken along the line 601 of FIG. 4. The acoustic elements 614 and the buffer elements 612 include a matching layer 680a, a piezoelectric layer 680b, a dematching layer 680c, and a bump layer 680d. The matching layer 680a matches the acoustic impedance of the piezoelectric layer 680b to that of the body being diagnosed. The piezoelectric layer 680b transmits ultrasound waves and receives echoes reflected off target tissue structures. The dematching layer 680c reflects backward ultrasound waves travelling from the backside of the piezoelectric layer 680b. The bump layer 680d includes flip-chip bumps 691. The matching layer 680a, the dematching layer 680c, and the bump layer 680d can be composed of suitable conductive materials. The piezoelectric layer 680b can be composed of lead zirconium titanate (PZT). The IC layer 326 includes bump pads 692 coupled to the flip-chip bumps 691. An underfill material 693 fills the region between the bump layer 680d and the IC layer 326. The outer edges of the array structure 600 can be plated with a metalized ground edge plating 710, which may be composed of any suitable conductive material (e.g., gold).

Referring to the step 330 of the method 300 and FIGS. 6 and 7, in an embodiment, at least a portion of the gaps 616 between the plurality of buffer elements 612 are filled with a sealing material 810. The ground edge plating 710 on top of the array structure 600 is not shown in FIG. 8 for clarity of illustration. For example, the sealing material 810 is applied around sides 630 of the array structure 600 and wicked into the gaps 616 between the plurality of buffer elements 612. The sealing material 810 can be a curable ultraviolet (UV) epoxy material or any suitable material. FIG. 6 shows the array structure 600 with the sealing material 810 surrounding the sides 630. FIG. 7 shows the sealing material 810 wicking or spreading into the gaps 616. The spreading is shown by the arrows in FIG. 7. The sealing material 810 is allowed to wick into a pre-determined portion of the gaps 616 (e.g., before reaching the air kerfs 618 and 620) as shown by the dotted lines 901. The pre-determined portion can vary in different embodiments. In some embodiments, the pre-determined portion includes a depth 930 of at least 20 jam from an outer-boundary of the buffer elements 612. In some embodiments, the sealing material 810 can be cured by applying a UV activating light to the sealing material before the sealing material reaches the air kerfs 618, 620. In other embodiments, the sealing material 810 can be cured by any suitable process, such as by applying heat, chemicals, and/or wavelengths of light other than ultraviolet light (e.g., visible light, infrared light, etc.).

Referring to the step 340 of the method 300 and FIG. 8, in an embodiment, the sealing material 810 filling the gaps 616 between the plurality of buffer elements 612 is cured such that the array of acoustic elements 614 remain spaced apart by the air kerfs 618 and 620. FIG. 8 shows that the sealing material 810 is spread into the gaps 616 reaching the pre-determined portion. The curing can include applying a UV light to stop the spreading or wicking of the sealing material 810 when the pre-determined portion is filled.

Referring to the step 350 of the method 300 and FIGS. 8 and 9, in an embodiment, excess sealing material 810 is removed, for example, by dicing along the dashed lines 1010 in FIG. 8. FIG. 9 shows the array structure 600 after the excess sealing material 810 is removed. In some embodiments, the remaining sealing material 810 can have a thickness 812 between about 20 µm to about 40 µm.

Referring to the step 360 of the method 300 and FIG. 10, in an embodiment, a ground plane 1230 is bonded to the top of the array structure 600 to form the imaging component. FIG. 10 illustrates a cross-sectional view of the imaging component including the array structure 600 taken along the line 1101 of FIG. 9. The ground plane 1230 can be a polyester film with gold metallization. Dimensions of the ground plane 1230 may vary in different embodiments. In some embodiments, the ground plane 1230 can have a thickness 1232 of about 5 µm. The ground plane 1230 provides an electrical ground return for the array structure 600. For example, the outer-most bump pads 692 are connected to ground connections 694 as shown in FIG. 10.

After forming the array, the array can be coupled to a probe housing, such as a head of the probe housing. An encapsulating material can be applied to the head of the probe housing to secure the array within the probe housing. The encapsulating material may include polydimethylsiloxane (PDMS), polyurethane, UV adhesives, or any suitable material that have desirable characteristics such as acoustic properties, bonding strength, and ease to work with during manufacturing.

The use of the sealing material 810 around the array structure 600 and partially filling the gaps 616 between the buffer elements 612 prevent the encapsulating material from wicking into the air kerfs 618 between the acoustic elements 614. As described above, the sealing material 810 can have a thickness 812 between about 20 µm to about 40 µm. Thus, the disclosed embodiments can create air-filled kerfs with a minimal increase in the size of the imaging component. For example, the disclosed embodiments can be applied to fabricate a transducer array for external ultrasound imaging, where a head of the ultrasound probe carrying the transducer array can be ergonomically positioned between ribs of the human body. In addition, the disclosed fabrication method is suitable for bulk production and automation.

In some aspects, rectangular ultrasound transducer arrays can pose challenges for an ultrasound technician. For example, in cardiac imaging (e.g., echocardiography), an external ultrasound probe may be positioned and precisely aligned between a patient's ribs to obtain images of the patient's heart. This can be difficult to do for an ultrasound probe that comprises a rectangular array of acoustic elements, because one or more corners of the array may restrict movement and alignment of the ultrasound probe between the patient's ribs and/or induce pain or discomfort for the patient during the imaging procedure. Accordingly, it may be beneficial to produce ultrasound imaging arrays that comprise non-rectangular shapes, or non-perpendicular shapes, that are advantageously ergonomic. Non-rectangular transducer arrays can be coupled to, or placed within, ergonomic, non-rectangular housings that can improve patient comfort during imaging procedures, as well as operator workflows. For example, because a non-rectangular array and/or housing can be more easily maneuvered in restricted locations, such as between the patient's ribs, the operator can more easily orient the probe to achieve the desired imaging plane, and with reduced discomfort to the patient.

Figure 11:
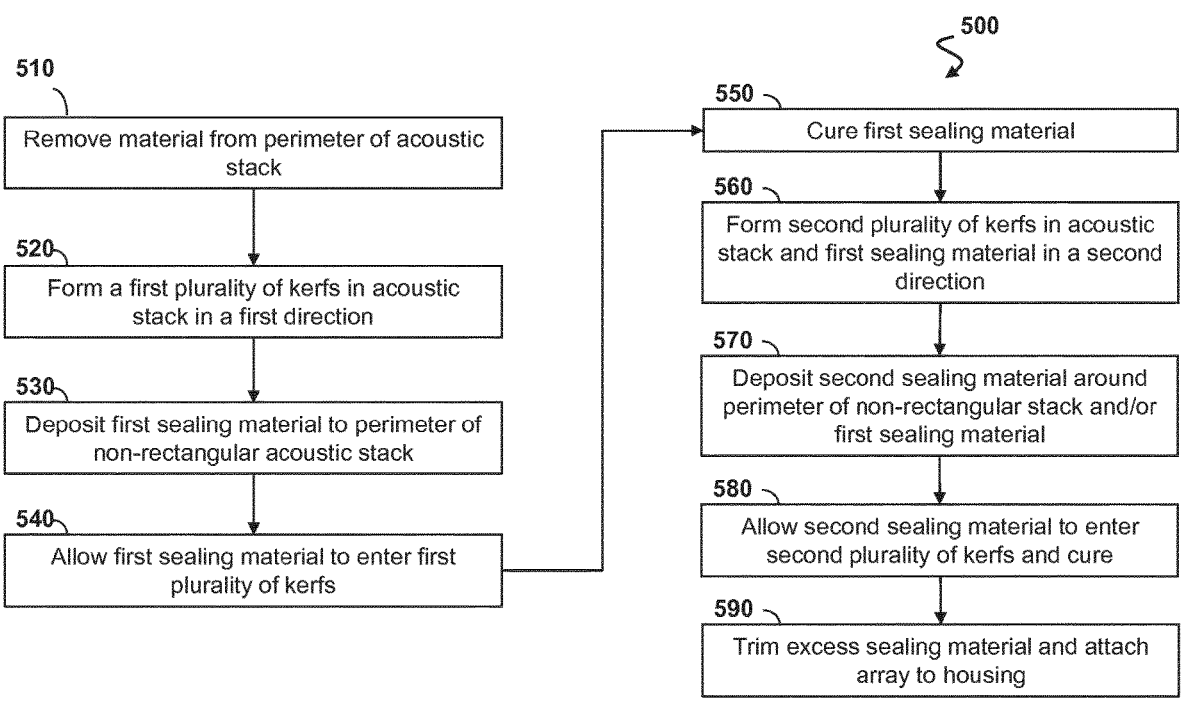
FIG. 11 is a flow diagram of a method for manufacturing a transducer array according to embodiments of the present disclosure.

However, producing two-dimensional arrays of acoustic elements that comprise non-rectangular shapes can be challenging. As will be explained further below, non-rectangular arrays will typically include some non-rectangular acoustic elements that are structurally unstable, and susceptible to breaking away from the acoustic stack. It is therefore desirable to employ manufacturing processes for producing non-rectangular arrays that avoid creating unstable acoustic elements that are likely to break off during assembly, or during an imaging procedure. FIGS. 11-17 illustrate a method for manufacturing an ergonomic, non-rectangular ultrasound transducer array, according to some aspects of the present disclosure. FIG. 11 is a flow diagram describing various steps of a method for manufacturing a non-rectangular transducer array, according to some aspects of the present disclosure. FIGS. 12-17 illustrate an acoustic stack 720 at various steps of the process detailed in FIG. 11.

Figure 12:
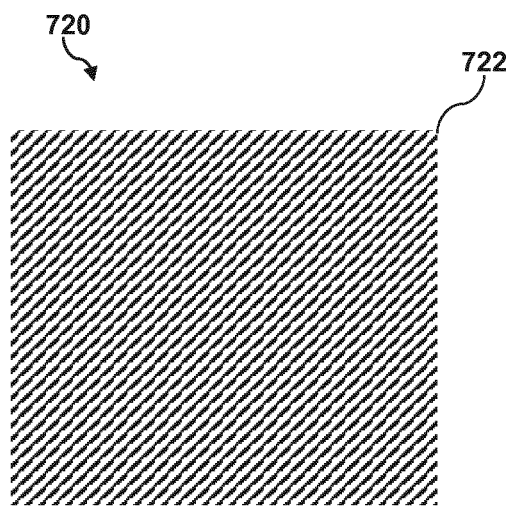
FIG. 12 is a top view of an acoustic stack in a stage of manufacturing according to embodiments of the present disclosure.
Figure 13:
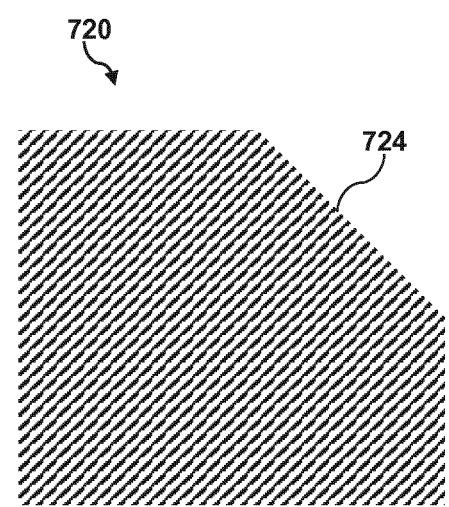
FIG. 13 is a top view of an acoustic stack in a stage of manufacturing according to embodiments of the present disclosure.

Referring to FIGS. 11-13 a rectangular acoustic stack 720 is provided (FIG. 12), and material is removed from a perimeter of the acoustic stack 720, such as from a corner 722 of the acoustic stack 720 (FIG. 13). It will be understood that, for illustrative purposes, FIG. 12 illustrates only a portion or area of the acoustic stack 720, rather than the entirety of the acoustic stack 720.

The acoustic stack 720 comprises a corner 722. As explained above, corners of rectangular arrays can present challenges in imaging procedures, particularly where a probe must be guided to and placed between bodily structures, such as the ribs. Accordingly, it may be beneficial to alter the shape, such as the perimeter, of the acoustic stack 720 to provide a more ergonomic design. As shown in FIGS. 12 and 13, the acoustic stack 720 can be made more ergonomic by removing material from the corner area 722 to produce a non-rectangular shape or perimeter. In step 510, material is removed from the corner area 722 to form a chamfered edge 724. In other embodiments, material can be removed by produce one or more curved segments and/or one or more polygonal shapes. For example, the shape of the acoustic stack 720 can be modified to include one or more of a chamfer, a bevel, a fillet, a round edge, or any combination of suitable geometric features. The material of the stack can be removed by, for example, cutting, dicing, grinding, etching, and/or by any other suitable shaping process. In some embodiments, the acoustic stack 720 is pre-formed to have a non-polygonal shape including any of the non-polygonal features described above such that no material needs to be removed from the acoustic stack 720 to create a non-polygonal shape.

Figure 18:
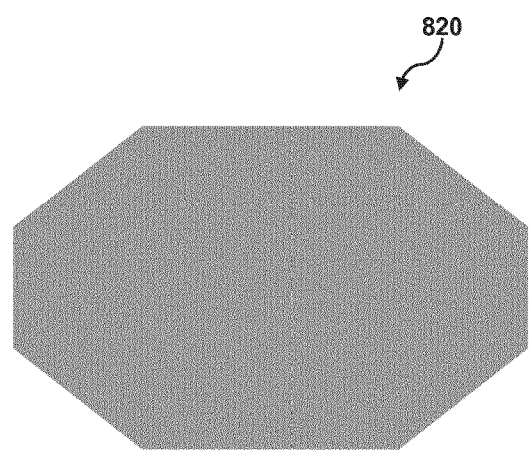
FIG. 18 is a top view of a non-rectangular acoustic stack according to embodiments of embodiments of the present disclosure.
Figure 19:
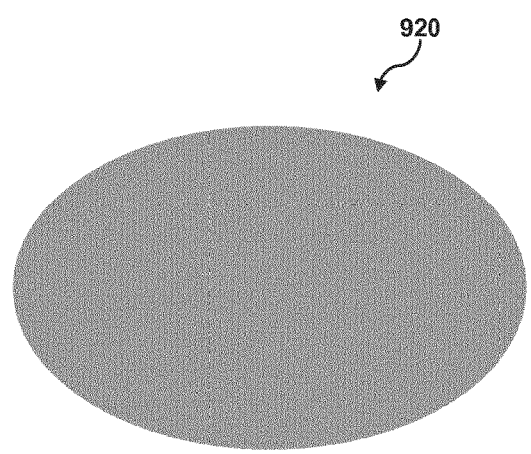
FIG. 19 is a top view of a non-rectangular acoustic stack according to embodiments of the present disclosure.

FIGS. 18 and 19 depict a polygonal transducer array 820, and a non-polygonal, ellipsoidal transducer array 920, respectively. Any suitable polygonal shape, ellipsoidal shape, regular shape, irregular shape, symmetrical shape, and/or non-symmetrical shape for the transducer array is contemplated. In that regard, it is understood that FIGS. 18 and 19 illustrate a profile or a top view of the transducer array, such as a length and a width. The transducer array is three-dimensional in that it also has a height or a depth (e.g., as shown in FIGS. 2, 5, and 10). In that regard, the transducer array can be described as a geometric prism in some instances. One or both of the transducer arrays 820, 920 can be formed according to the method 500 set forth in FIG. 11. For example, the transducer arrays can be formed by removing material form the corners of a rectangular acoustic stack, or forming the acoustic stacks 820, 920 to have non-rectangular shapes without the need to remove material.

Referring again to FIGS. 11-13, in some embodiments, the non-rectangular acoustic stack 720 can be coupled, attached, or otherwise joined to a processor chip, or a computer chip, such as an ASIC. In some aspects, the computer chip can be described as an integrated circuit (IC), or IC layer. The computer chip, or IC layer, can comprise a similar or identical shape as the non-rectangular acoustic stack 720. In that regard, in some embodiments, step 510 comprises simultaneously removing material from the rectangular acoustic stack 720 and a rectangular computer chip, such that the shapes of the acoustic stack 720 and the computer chip align. This can be performed before or after attaching the computer chip to the acoustic stack 720. In other embodiments, the acoustic stack 720 and computer chip are shaped separately. The computer chip can include integrated logics and/or circuitries formed from a semiconductor material, such as silicon. The integrated logics and/or circuitries are configured to multiplex control signals, for example, generated by the processor 28 shown in FIG. 1, and transfer the control signals to corresponding acoustic elements of an array. The controls signals can control the emission of ultrasound pulses and/or the reception of echo signals. In the reverse direction, the integrated logics and/or circuitries are configured to receive ultrasound echo signals reflected by target tissue and received by the acoustic elements. The integrated logics and/or circuitries convert the ultrasound echo signals into electrical signals and transfer the electrical signals through an interposer and an electrical cable 16 to the processor 28 for processing and/or display. The integrated logics and/or circuitries can be further configured to perform signal conditioning before transferring the signals. Signal conditioning may include filtering, amplification, and beamforming. In some embodiments, the computer chip may have a longer length than the acoustic stack 720 for coupling to an interposer.

Figure 14:
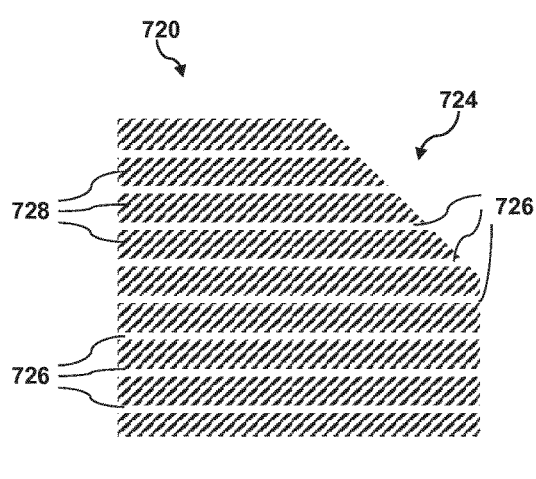
FIG. 14 is a top view of an acoustic stack having a plurality of kerfs in a stage of manufacturing according to embodiments of the present disclosure.

In step 520, and as shown in FIG. 14, the acoustic stack 720 is diced, cut, ground, etched, or otherwise machined to form a first plurality of kerfs 726, which may also be described as gaps or spaces. The kerfs 726 are parallel and are formed in a first direction (horizontal) to separate a plurality of acoustic stack segments 728. Although explained in terms of dicing, any process described above can be used to create the kerfs 726, such as cutting and/or etching. In some embodiments, photolithography techniques can be used to create the kerfs 726. In the illustrated embodiment, the kerfs 726 comprise air kerfs, meaning kerfs or channels that separate individual acoustic stack segments 728 or acoustic elements by air. In other embodiments, the kerfs 726 can be filled with a material, such that individual acoustic stack segments 728 and/or acoustic elements are separated from one another by the material.

Particularly when air kerfs are used, such as in the acoustic stack 720 of FIG. 14, it may be beneficial to provide a seal for the air kerfs 726 so that a foreign material (e.g., ultrasound gel, water, cleaning solution) does not find its way into the kerfs 726 of the acoustic stack 720. Accordingly, in step 530, shown in FIG. 15, an edge seal 730 comprising a first sealing material 732 is applied around a perimeter of the acoustic stack 720 to seal the kerfs 726, such that the first sealing material 732 is in direct contact with the non-rectangular perimeter of the acoustic stack 720. The first sealing material 732 includes a first plurality of penetrating sections 734 partially disposed within the kerfs 726. In step 540, the penetrating sections 734 are formed by allowing the first sealing material 732 to enter into the first plurality of kerfs 726 by a certain distance, and in step 550, the first sealing material 732 is cured. For example, the first sealing material 732 may comprise a curable adhesive, potting material, or other fluidic material that can flow between kerfs 726. In one embodiment, the first sealing material 732 comprises an epoxy or curable adhesive that can be cured by, for example, ultraviolet (UV) light, heat, air exposure, or any other suitable method. In some aspects, the process for forming the penetrating sections 734 can include waiting a pre-determined amount of time and/or waiting for the first sealing material 732 to advance a pre-determined distance into the kerfs 726, and activating a curing process (e.g., applying UV light) to cure and/or solidify the first sealing material 732, such that the first sealing material 732 ceases to advance into the kerfs 726 within the acoustic stack 720. For example, in some embodiments, the first sealing material may be allowed to advance, or wick, into the kerfs 726 for a period of about 1 second to about 30 seconds. The amount of time allowed for the first sealing material to wick into the acoustic stack 720 may depend on the viscosity of the pre-cured sealing material. In some embodiments, the first sealing material 732 may be allowed to advance into the acoustic stack 720 between about 150 µm and about 1 mm, including between about 250 µm and about 350 µm. In some embodiments, the sealing material 732 may be allowed to advance into the acoustic stack 720 by a distance corresponding to a width of each acoustic stack segment 728 and/or acoustic element, such as a width corresponding to one half of an acoustic element, one acoustic element, two acoustic elements, etc.

Figure 15:
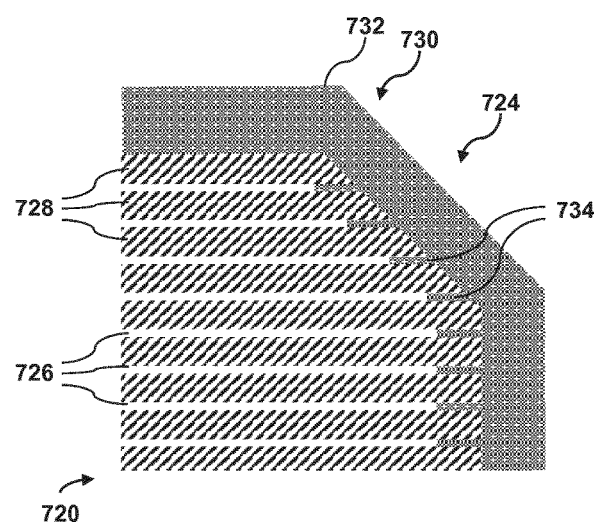
FIG. 15 is a top view of an acoustic stack having a plurality of kerfs and a sealing material at a perimeter in a stage of manufacturing according to embodiments of the present disclosure.
Figure 16:
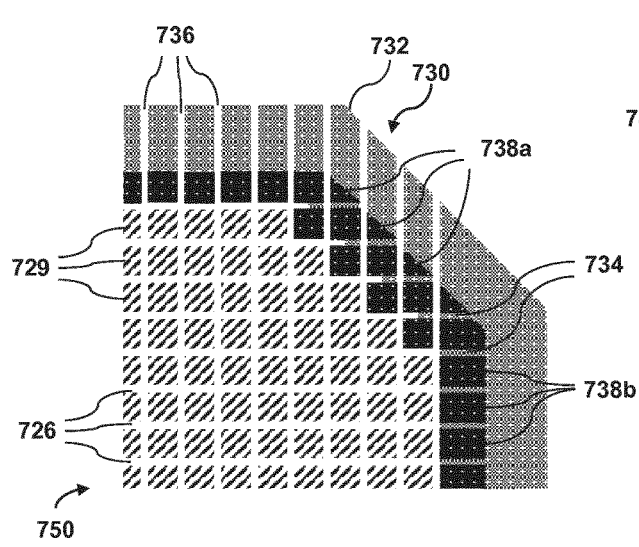
FIG. 16 is a top view of an array structure formed of an acoustic stack in a stage of manufacturing according to embodiments of the present disclosure.
Figure 17:
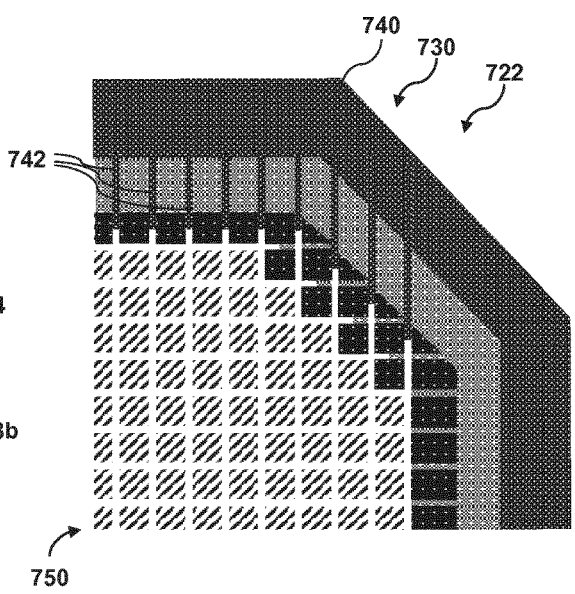
FIG. 17 is a top view of an array structure formed of an acoustic stack in a stage of manufacturing according to embodiments of the present disclosure.

With reference to FIGS. 11 and 15, in step 560 a second plurality of kerfs 736 is formed in the acoustic stack 720 in a second direction (vertical). In that regard, in the embodiment, of FIG. 15, the direction of the second plurality of kerfs 736 is perpendicular to the direction of the first plurality of kerfs 726. Forming the second plurality of kerfs 736 divides the acoustic stack segments 728 shown in FIGS. 12 and 13 into a two dimensional array 750 of acoustic elements, wherein the array 750 comprises active elements 729 and buffer elements 738. Buffer elements 738 may be described as acoustic elements of the array 750 that are inactive. For example, buffer elements 738 may be considered inactive due to mechanical restriction by sealing material 732 disposed between and/or around the buffer elements 738, electrical connections or a lack thereof that prevent the buffer elements 738 from being driven to emit and receive ultrasound energy, or both. In other words, although the buffer elements 738 are formed from the same acoustic stack 720 as the active elements 729, the buffer elements 738 are considered inactive or inert.

The buffer elements 738 are positioned at or near the perimeter of the array 750. A first portion 738a of the buffer elements in the acoustic stack of FIG. 14 comprise non-rectangular shapes or profiles (e.g., triangular), and are located at or near the chamfered edge 724 of the array 750. The chamfered edge 724 comprises a portion of the perimeter of the array 750. A second portion 738b of the buffer elements comprises rectangular shapes or profiles. One or more buffer elements of the second portion 738b may be spaced from the outer perimeter of the array by one or more other buffer elements, while the buffer elements of the first portion 738a are positioned at the perimeter of the array 750, or directly adjacent the perimeter. In some aspects, the buffer elements 738 can be described as forming the perimeter or edge of the array 750.

As mentioned above, some of the buffer elements, particularly the first portion 738a of the buffer elements may be unstable without the reinforcement of the first sealing material 732. Thus, applying the first sealing material 732 before forming the second plurality of kerfs 736 can add support and reinforcement to the buffer elements 738 located at or near the outer perimeter or outer edge of the array 750, particularly the buffer elements of the first portion 738a that comprise non-rectangular cross sections and/or are more susceptible to breaking away from the array 750.

In step 570, a second sealing material 740 is deposited over, or in addition to, the cured first sealing material 732, such that the second sealing material 740 at least partially penetrates or enters the second plurality of kerfs 736 to seal the second plurality of kerfs 736 of the transducer array 750. As with the first sealing material, in step 580, the second sealing material 740 is allowed to advance within the second plurality of kerfs 736 to form a second plurality of penetrating portions 742. The second sealing material 740 may comprise the same type of material as the first sealing material 732, or may comprise a different material. The second sealing material 740 may comprise a separate layer of material disposed over, or surrounding the first sealing material 732. In other embodiments, the second sealing material 740 may not be applied and cured. For example, in some embodiments, a wrap is applied around the transducer array 750, instead of the second sealing material 740.

In step 590, excess sealing material from the first and/or second sealing materials 732, 740 is trimmed, cut, diced, ground, or otherwise removed, leaving the first and second penetrating portions 734, 742 in place to seal the array 750 and/or stabilize the buffer elements near the perimeter of the array 750. The array 750 is then attached to a housing, for example within a head of the probe housing. The housing can be an external ultrasound probe, ICE catheter, TEE probe, IVUS catheter, TTE probe, or any array-based ultrasound device. As explained above, the array 750 can be attached to the probe housing using a filling adhesive and/or potting material. Because the array 750 comprises a non-rectangular shape, the array 750 may fit within a more ergonomically designed probe housing such that the probe can be more easily maneuvered and placed to obtain an ultrasound image. For example, the non-rectangular probe may be more easily maneuvered to obtain images between the ribs of a patient.

It will be understood that other processing steps may be performed in addition to those described with respect to FIGS. 11-17. For example, in one embodiment, a third sealing material may be applied in the first and second pluralities of kerfs 726, 736 between the active acoustic 729 elements and/or the buffer elements 738, displacing the air in the kerfs 726, 736. The third sealing material may comprise an acoustically compatible material configured to allow for activation and use of individual elements of the array 750. In some embodiments, an acoustic matching layer and/or a ground plane (e.g., 210, 220, FIG. 2) can be attached to top side of the array 750. The acoustic matching layer and/or the ground plane can function with the edge seal 730 to seal the array 750. It will also be understood that one or more steps, features, and/or components described with respect to FIGS. 2-10 can be used in conjunction with the steps, features, and/or components described with respect to FIGS. 11-17.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An ultrasound imaging device, comprising:
an array of acoustic elements comprising a non-rectangular perimeter, wherein the array of acoustic elements further comprises:
a plurality of active elements configured to emit ultrasound energy and receive echoes corresponding to the emitted ultrasound energy;
a plurality of buffer elements surrounding the plurality of active elements at the non-rectangular perimeter of the array of acoustic elements; and
an edge seal comprising sealing material positioned at least partially around the plurality of buffer elements, wherein the edge seal comprises:
a first sealing material in direct contact with the non-rectangular perimeter of the array of acoustic elements, the first sealing material comprising a plurality of kerfs, and
a second sealing material positioned around the first sealing material and disposed within the plurality of kerfs of the first sealing material,
wherein a buffer element of the plurality of buffer elements is spaced from at least one other buffer element by the sealing material of the edge seal.

2. The device of claim 1, wherein the non-rectangular perimeter comprises a curved segment.

3. The device of claim 1, wherein the non-rectangular perimeter comprises a polygon.

4. The device of claim 1, wherein each buffer element of a first portion of the plurality of buffer elements comprises a non-rectangular profile, the first portion of the plurality of buffer elements at an outer edge of the array of acoustic elements.

5. The device of claim 4, wherein each buffer element of a second portion of the plurality of buffer elements comprises a rectangular profile, the second portion of the plurality of buffer elements spaced from the outer edge of the array of acoustic elements.

6. The device of claim 1, further comprising a processor chip coupled to a surface of the array of acoustic elements, wherein the processing chip comprises a non-rectangular perimeter that aligns with the non-rectangular perimeter of the array of acoustic elements.

7. The device of claim 1, further comprising a housing, wherein the array of acoustic elements is coupled to the housing.

8. A method of manufacturing the ultrasound imaging device according to claim 1, comprising:
- removing material from a perimeter of an acoustic stack such that the acoustic stack comprises a non-rectangular perimeter;
- forming a first plurality of kerfs in the acoustic stack in a first direction;
- depositing a first sealing material at the non-rectangular perimeter of the acoustic stack;
- allowing the first sealing material to enter the first plurality of kerfs;
- curing the first sealing material; and
- forming a second plurality of kerfs in the acoustic stack and the first sealing material in a second direction to form an array of acoustic elements;
- depositing a second sealing material around the first sealing material;
- allowing the second sealing material to enter the second plurality of kerfs; and
- curing the second sealing material.

9. The method of claim 8, wherein removing material from the perimeter of the acoustic stack comprises forming a curved segment.

10. The method of claim 8, wherein removing material from the perimeter of the acoustic stack comprises forming a polygonal segment.

11. The method of claim 8, wherein allowing the first sealing material to enter the first plurality of kerfs comprises waiting for the first sealing material to advance between about 150 microns and about 250 microns into the acoustic stack.

12. The method of claim 11, wherein the first sealing material comprises an epoxy, and wherein curing the first sealing material comprises directing ultraviolet light to the epoxy.

13. The method of claim 8, further comprising:
- removing material from a processing chip such that the processing chip comprises a non-rectangular perimeter; and
- coupling the processing chip to the acoustic stack such that the non-rectangular perimeter of the processing chip aligns with the non-rectangular perimeter of the acoustic stack.

14. The method of claim 8, further comprising coupling the array of acoustic elements to a housing.

* * * * *